United States Patent [19]

Huey et al.

[11] 4,274,826
[45] Jun. 23, 1981

[54] DENTURE ADJUSTMENT TOOL

[76] Inventors: Elbert P. Huey, 4714 E. Lafayette Blvd., Scottsdale, Ariz. 85018; Adrian W. Craig, 6703 E. McDonald Dr., Scottsdale, Ariz. 85253

[21] Appl. No.: 85,896

[22] Filed: Oct. 18, 1979

[51] Int. Cl.³ .............................................. A61C 3/06
[52] U.S. Cl. .................................. 433/144; 433/142; 30/294; 7/158; 29/78
[58] Field of Search .............. 433/144, 142, 143, 141; 30/294, 314, 315, 26, DIG. 8; 168/48; 132/76.4, 76.5, 75.6; 7/158, 169; 29/78; D24/11

[56] References Cited

U.S. PATENT DOCUMENTS

| 51,519 | 12/1865 | Reed | 7/158 |
|---|---|---|---|
| 273,821 | 3/1883 | Crosthwaite | 433/144 |
| 368,198 | 8/1887 | Eaton | 30/26 |
| 448,409 | 3/1891 | Cassidy | 132/76.4 |
| 778,650 | 12/1904 | Forquignon | 433/144 |
| 1,345,721 | 7/1920 | Wallace | 7/158 |
| 4,109,384 | 8/1978 | Dorian | 433/147 |

FOREIGN PATENT DOCUMENTS 8964 of 1886 United Kingdom ...................... 30/294

*Primary Examiner*—F. Barry Shay
*Assistant Examiner*—John J. Wilson
*Attorney, Agent, or Firm*—Cahill, Sutton & Thomas

[57] ABSTRACT

A claw having a sharp edged tip is disposed at the extremity of a handle supported shank. The configuration of the tip provides a cutting edge adapted for removing denture material in confined as well as open areas of a denture. The surfaces of the shank, including at least a side surface of the claw, are abrasive for grinding and smoothing surfaces of the denture.

2 Claims, 3 Drawing Figures

DENTURE ADJUSTMENT TOOL

The present invention relates to dental implements and, more particularly, to denture adjustment tools.

In the field of professional and personal dental care, various tools have been developed for contouring teeth and dentures. U.S. Pat. No. Des. 53,958, describes a hand-held tool having trimming files set at opposed ends of a handle. U.S. Pat. No. 522,211 is directed to a tool of elongated sheet metal stiffened by a rib and having saw teeth disposed along one longitudinal edge and an abrading surface parallel to an opposed longitudinal edge. U.S. Pat. No. 1,138,479 is directed to a strip of cellulose material having different abrading surfaces disposed on opposed sides thereof. U.S. Pat. No. 1,316,685 illustrates a tool and tool holder wherein the tool includes a flexible pointed scraper for insertion intermediate the root of a tooth and the adjacent gum. U.S. Pat. No. 4,030,198 is directed to a tool suspending in tension a double surfaced strip of abrasive material for stripping tooth enamel. U.S. Pat. No. 2,929,143 describes flexible abrasive material for placement between the upper and lower sets of natural or artificial teeth to abrade high spots upon working the sets of teeth against one another.

Dental prosthetic devices, such as dentures, are fitted as well as possible in the dentist's office. Nevertheless, a perfect fit is seldom achieved without one or more follow-up visits. The subsequent visits are necessarily time consuming for both the patient and the dentist and incur certain expenses. Usually, the modifications in fit that need to be made during the follow-up visits are relatively minor and could readily be performed by the patient himself/herself if an appropriate tool were available and the patient taught how to use it. None of the devices described above nor any others known to applicant are readily useable by the patient for these purposes without extensive training; moreover, tools which might be used for these purposes are intended for and adapted to other functions and therefore constitute a compromise.

A tool useable by a patient to adjust his/her dentures must possess certain characteristics in order to be feasible and useable by an untrained person. It must have a cutting element which is useable in confined areas. It must have an abrasive surface for grinding or polishing both broad and limited areas. And, these characteristics should be combined in a single hand-held tool for ease of use and reduction in expense.

It is therefore a primary object of the present invention to provide a tool for adjusting dentures.

Another object of the present invention is to provide a tool for adjusting the bite of dentures.

Yet another object of the present invention is to provide a tool for cutting and grinding a denture to improve its fit.

Still another object of the present invention is to provide a tool for adjusting dentures, which tool includes both cutting and abrading elements.

A further object of the present invention is to provide a hand-held tool for adjusting dentures.

A yet further object of the present invention is to provide an inexpensive denture adjustment tool.

A still further object of the present invention is to provide a tool for adjusting dentures which is readily useable by unskilled persons having a reasonable degree of manual dexterity.

These and other objects of the present invention will become apparent to those skilled in the art as the description thereof proceeds.

The present invention may be described with greater specificity and clarity with reference to the following drawings, in which.

Figure 1:
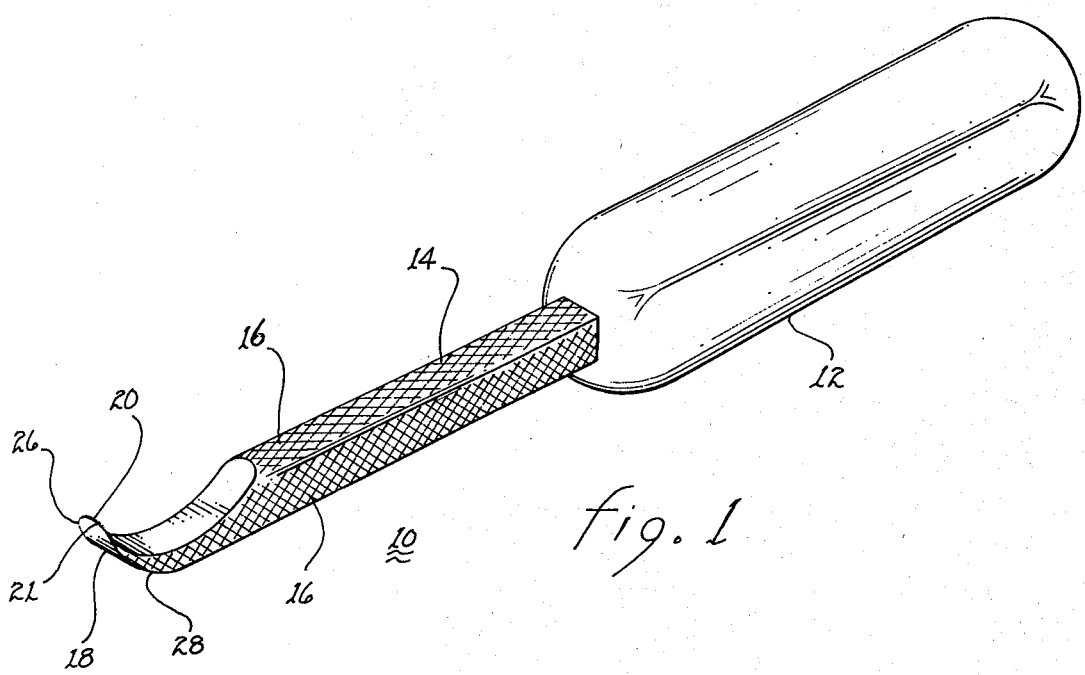
FIG. 1 is a perspective view of the denture adjustment tool.

Referring to FIG. 1, there is illustrated a denture adjustment tool 10 useable by individuals to modify the contours of selected parts of their dentures or other dental prosthetic devices. The tool includes a handle 12 of reasonably large cross-section to provide a good grip for the user. A shank 14 extends from the handle, which shank includes abrasive surfaces 16 for grinding, filing or polishing the parts of the denture being worked upon. A claw 18 is disposed at the terminal end of shank 14. The claw includes a sharpened edge 20 extending from tip 21 of the claw along each side 26, 28, for cutting material away from parts of the denture.

Figure 2:
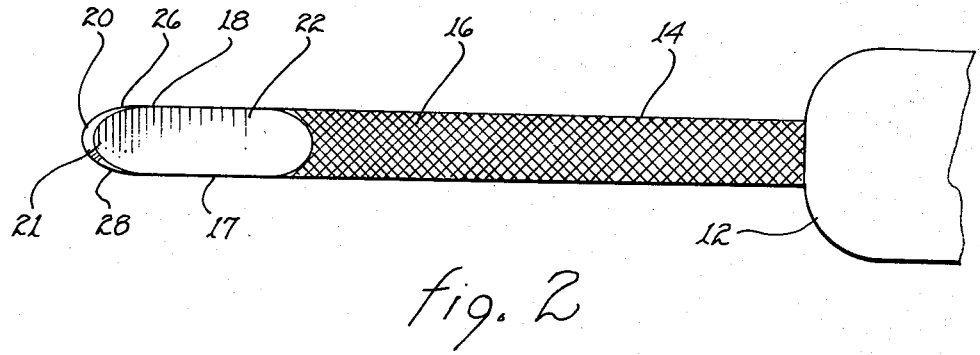
FIG. 2 is a top view thereof.
Figure 3:
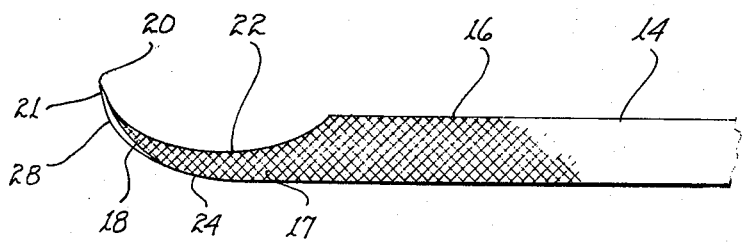
FIG. 3 is a side view thereof.

Turning to FIGS. 2 and 3, tool 12 will be described in further detail. Presently, it is contemplated that shank 14 will have a square cross-section and thereby present a plurality of planar surfaces 16, all of which may be abrasive and of the same coarseness; alternatively, each surface may have a different coarseness such that one surface may be used primarily for grinding while another surface may be used primarily for polishing. It is to be understood that all or part of one of surfaces 16 may be convex or concave to provide a curved surface for grinding or polishing a segment of the denture.

Claw 18 is tapered in height throughout its length to provide a varying width abrasive surface 17. Such variable width abrasive surface provides the user with the capability of grinding or polishing a very limited area of the denture. Moreover, it permits insertion of the abrasive surface into confined spaces otherwise inaccessible to the major portion of shank 14. The claw is also tapered in width toward its extremity to provide a sharp curve at tip 21 or apex of edge 20. Edge 20, being ground to a cutting edge and curved as described, provides wide latitude in deployment of the cutting edge in confined areas of the denture.

The use of a curved tapered claw rather than a straight taper at the extremity of shank 14 provides several benefits. Concave surface 22 in conjunction with convex surface 24 tends to facilitate positional movement of the claw tip by requiring a lesser degree of manual dexterity to accurately control the movement of the tool than would be required were the tapered tip simply a longitudinal extension of the handle. Moreover, surfaces 22 and 24 may be used to help support the tool upon an adjacent surface of the denture while edge 20 is slid to perform a cutting function. From the drawings, particularly FIG. 3, it may be noted that the tip 21 or apex of the claw is located substantially closer to the longitudinal axis of shank 14 because of the orientation of curved surfaces 26 and 24 than would be the case were the claw to extend directly laterally from the shank without the undercut presented by concave surface 22. Such positioning of the tip aids in accurate manipulation of the tool and requires a lesser degree of manual dexterity.

Any patient with normal manual dexterity can be quickly and easily taught by a dentist or his technician how to use tool 10 to make minor adjustments or newly fitted dentures. Thereby, the patient can obviate the expense and time attendant a trip to the dentist's office for a slight adjustment necessitated by an initial or later developed problems in the bite of a denture.

Because the tool is relatively simple and is capable of being manufactured at relatively low cost, it is clearly cost effective, when compared to the time and expense associated with two or more trips to a dentist's office.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

We claim:

1. A one piece multi-function manual denture adjustment tool, said tool comprising in combination:

(a) a handle for gripping said tool;
   (b) a shank square in cross-section and extending from said handle, said shank including an abrasive surface disposed on the sides of said shank; and
   (c) a dual tapered claw disposed at the extremity of said shank, said claw including a terminal tip and a curved cutting edge extending from either side of said tip toward said shank, said claw further including two opposed sides of widths diminishing toward said tip and defining the curvature of said claw, said diminishing width opposed sides having abrasive surface and being extensions of respective ones of said abrasive sides of said shank to define variable width abrasive surfaces.

2. The tool as set forth in claim 1 wherein said claw includes further opposed sides converging toward one another to define said terminal tip at the point of convergence, one of said further opposed sides being convex and another of said opposed sides being concave.

* * * * *